United States Patent
Hodgson et al.

(10) Patent No.: US 6,201,885 B1
(45) Date of Patent: Mar. 13, 2001

(54) METHOD FOR BAKERY PRODUCT MEASUREMENT

(75) Inventors: Allan S. Hodgson, Saint Anne, IL (US); Catherine R. Barrow, Munster; Jessica M. Arnold, Pendleton, both of IN (US)

(73) Assignee: Bunge Foods Corporation, St. Louis, MO (US)

( * ) Notice: Subject to any disclaimer, the term of this patent is extended or adjusted under 35 U.S.C. 154(b) by 0 days.

(21) Appl. No.: 09/152,230

(22) Filed: Sep. 11, 1998

(51) Int. Cl.[7] .................................................. G06F 15/46

(52) U.S. Cl. ........................ 382/110; 382/165; 382/100; 382/156; 348/89; 209/576; 209/643; 209/702; 364/555

(58) Field of Search .................................. 209/508, 556; 235/92; 364/555, 552; 382/110

(56) References Cited

U.S. PATENT DOCUMENTS

| | | | |
|---|---|---|---|
| 3,575,287 | 4/1971 | Graveley . | |
| 3,805,028 | * 4/1974 | Morton | 235/92 |
| 4,324,335 | 4/1982 | Conway et al. | 209/586 |
| 4,515,275 | 5/1985 | Mills et al. | 209/557 |
| 4,531,292 | 7/1985 | Pasternak | 33/18.1 |
| 4,687,107 | * 8/1987 | Brown et al. | 209/556 |
| 4,702,535 | 10/1987 | Beun | 312/308 |
| 4,713,781 | * 12/1987 | Brizgis et al. | 364/552 |
| 4,735,323 | 4/1988 | Okada et al. | 209/582 |
| 4,818,380 | 4/1989 | Azegami et al. | 209/565 |
| 4,940,536 | 7/1990 | Cowlin et al. | 209/592 |
| 4,975,863 | * 12/1990 | Sistler et al. | 364/555 |
| 5,060,290 | 10/1991 | Kelly et al. | 382/110 |
| 5,206,918 | 4/1993 | Levene | 382/110 |
| 5,212,637 | 5/1993 | Saxena | 600/407 |
| 5,301,090 | 4/1994 | Hed | 362/558 |
| 5,344,046 | 9/1994 | Maladanis et al. | 192/66 |
| 5,409,119 | * 4/1995 | Datari | 209/580 |
| 5,435,641 | 7/1995 | Dupuis et al. | 312/223 |
| 5,444,480 | 8/1995 | Sumita | 348/127 |
| 5,533,628 | 7/1996 | Tao | 209/580 |
| 5,574,251 | 11/1996 | Sevier | 174/50 |
| 5,659,624 | 8/1997 | Fazzari et al. | 302/110 |
| 5,659,819 | 8/1997 | LeCover | 396/164 |
| 5,732,147 | 3/1998 | Tao | 382/110 |
| 5,818,953 | 10/1998 | Queisser et al. | 382/110 |

FOREIGN PATENT DOCUMENTS 2279875    12/1987   (JP) .

OTHER PUBLICATIONS

Davidson et al, Fuzzy methods for automated inspection of food products, University of Guelph, Canada, pp. 909–913, 1999.*

McConnell et al, Color classification of non uniform baked and roasted foods. Food and process Engineering institute St. Joseph, M I 49085, Apr. 7, 1997..*

"CrumbScan Baked Product Evaluation, AIB Computer Software Brings Objectivity to Crumb Grain Evaluation", American Institute of Banking brochure (publication date unknown).

Rogers et al., "Development of an Objective Crumb–Grain Measurement", *Cereal Foods World,* vol. 40, No. 7, pp. 498–501 (Jul. 1995).

* cited by examiner

Primary Examiner—Matthew C. Bella
Assistant Examiner—Mahmood Choobin
(74) Attorney, Agent, or Firm—Cook, Alex, McFarron, Manzo, Cummings & Mehler, Ltd.

(57) ABSTRACT

The computer imaging analysis of bakery products for quality control and other purposes is disclosed. Apparatus and methods useful in such analysis are disclosed. The methods are useful on all types of bakery products. They can be used to analyze for parameters, such as size, shape, area and volume. They can also be used to analyze holes, grain or crust. Viewable images may be provided. The parameters can be compared with prescribed specifications and can be used on a plurality of products to determine substantial uniformity.

23 Claims, 7 Drawing Sheets

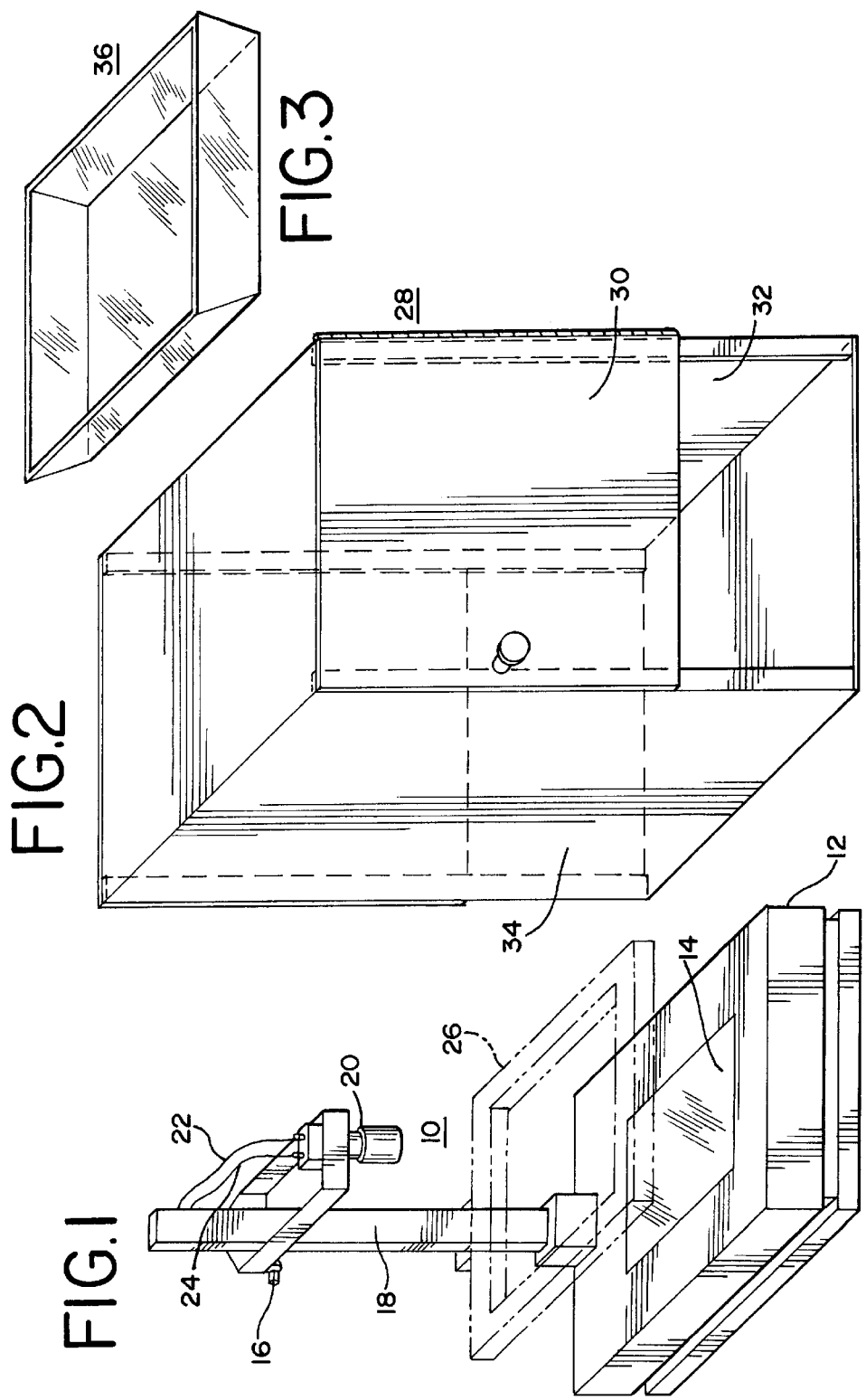

METHOD FOR BAKERY PRODUCT MEASUREMENT

FIELD OF THE INVENTION

The present invention concerns the measurement of bakery products using a computer imaging system.

BACKGROUND OF THE INVENTION

The production of large quantities of bakery products, such as cakes, donuts, muffins, pastries, and breads, in wholesale or retail bakeries requires that the products are consistent and essentially identical to meet the expectations of the customers. The bakery products are frequently made from prepared mixes and baked or cooked in a variety of equipment. To ensure the products meet prescribed specifications, they can be measured to characterize selected parameters, such as the size, shape, area, volume, grain size or shape, crust thickness, etc. to ensure that they meet acceptability criteria.

These physical characteristics of bakery products are critical for customer acceptance of the product and also may describe the quality of the product. One current test for round cake volume is known as the "Rapeseed Volume Test". This test involves placing a cake in a chamber, closing the chamber, inverting the measurement device to permit rapeseeds to surround the cake in the chamber and then measuring the displacement of the cake on a scale. The cake volume is an important measure which can be related to quality of the baked item. However, the Rapeseed Volume Test has been shown to have wide variability. It is difficult to obtain consistent results, particularly with different operators, as the test is particularly technique dependent.

Other tests involve size measurements with a ruler which can be time consuming and lack precision. The height/spread test currently practiced for muffins consists of placing three muffins on a ruler, peak side up, and measuring the spread. Then the muffins are turned on their side and the height of the three muffins is measured. Shape is described.

Grain development in a cake is related to eating characteristics and is often measured by observation and descriptive terms, e.g., tight, open, closed, tunnels, tornados, etc. A definitive numerical measurement would permit a greater and clearer definition of the grain structure of baked items.

Computer imaging is believed to have many advantages in measuring attributes of baked products. A camera image can be analyzed by computer software and measurements compared to preselected criteria. The measured attributes of bakery products can be used to define the quality of the item. It is proposed that the methods described herein can be used as a quality assurance tool on bakery products to ensure uniformity, consistency and provide accurate and precise measurements. These methods can also be used to provide objective measurements of bakery product characteristics, such as grain size and shape, instead of the subjective descriptors currently used.

Other objects and advantages of the present invention will become apparent as the description proceeds.

SUMMARY OF THE INVENTION

The present invention uses computer imaging to characterize and measure bakery products. The invention includes a method for determining the approximate volume of a bakery product using computer imaging. A bakery product is placed in a lighted field. The field is lighted in such a manner that there is sufficient contrast between the bakery product and the supporting surface on which it is placed that computer imaging software may distinguish between the bakery product and the supporting surface. An image from which the area of the bakery product can be determined is captured. A vertical slice is made in the bakery product and the vertical slice is placed in the lighted field. An image of the vertical slice of the bakery product is captured. The volume of the bakery product determined using the captured images is calculated. The illustrative embodiment of this method of determining approximate volume relates to its use on bakery products such as certain types of cakes.

This invention includes a method for determining the size and shape of a bakery product. In this method, at least one vertical slice is made. The vertical slice is placed in a lighted field. The lighting is such that there is sufficient contrast between the bakery product and the supporting surface so that computer imaging software may distinguish between the bakery product and the supporting surface in captured images. An image of the vertical slice of the bakery product is captured. Using this captured image, the length of the major axis, the length of the minor axis, area and roundness are determined and the square of the perimeter divided by the area is calculated. This method is well-suited for use on bakery products such as muffins.

This invention includes a method for determining the grain of a bakery product. A slice is made in the bakery product in such a manner as to expose the internal grain. The exposed internal grain is illuminated in such a manner that computer imaging software may distinguish grain holes. An image of the exposed internal grain is captured. The porosity (area of grain holes/total area) of the bakery product is calculated. The image may also be used to determine the sizes and shapes of grain holes. This method is suited for use with bakery products such as cakes, donuts, muffins, pastries and breads.

This invention includes a method for determining the area of holes and crust of a bakery product. A slice is cut at or near the midsection of a bakery product. A cut surface of the slice is illuminated in such a manner that computer imaging software may distinguish holes and crust. An image of the cut surface of the slice is captured. The area of the holes and the crust of the bakery product are determined. These areas can be reported as percentages of the total area measured or as percentages of the total area of the bakery product. The method can also be used to determine the sizes and shapes of the holes and the thickness of the crust.

This invention includes a method for analyzing a donut using computer imaging. A horizontal image of a donut or a horizontal slice of a donut is captured. Using the captured image, the diameter, area and area of the donut hole are calculated. If an image of a horizontal slice of a donut is used, the area of the holes within the donut may be calculated.

In the illustrative embodiments of each of these methods, a viewable image of the captured image of the bakery product is provided. These images can be stored by the computer or printed.

The present methods are anticipated to be quite useful for quality control purposes. These methods can be used to determine that bakery products meet prescribed specifications for the attributes determined and calculated using the methods. And, the methods include performing the steps on a plurality of bakery products to determine whether they meet prescribed specifications and are substantially uniform.

A more detailed explanation of the invention is provided in the following description and claims, and is illustrated in the accompanying drawings.

BRIEF DESCRIPTION OF THE DRAWINGS

FIGS. 1–5 comprise drawings of oppositions useful in the practice of the invention.

FIG. 1 is a perspective view of a light box, camera mount and camera;

FIG. 2 is a cabinet;

FIG. 3 is a sample tray;

DETAILED DESCRIPTION OF THE ILLUSTRATIVE EMBODIMENTS

Figure 4A:
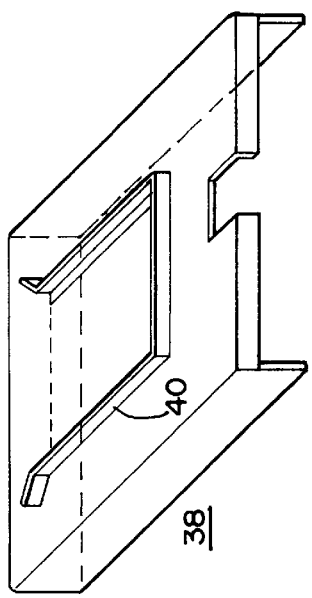
FIG. 4A is a front perspective drawing of a light box cover with a sample tray guide frame and FIG. 4B is a rear perspective drawing of the same apparatus.

Referring to FIG. 1, imaging apparatus 10 is shown. The light box 12 consists of a metal box with an adjustable light source in the lower part of the device. The light source consists of several light bulbs of different wattage with the light intensity controlled by dimmer switches. The light can be varied from fully off to the full power of the light source. A second light source, shown in phantom lines in FIG. 1, includes an incident light source in a cutout rectangular frame 26. This is mounted to be vertically adjustable.

In the presently preferred apparatus, inside the light box 12 are four 12 inch long 8 watt fluorescent bulbs and one, 8 inch diameter 22 watt circular bulb. The vertically adjustable incident light source consists of two, 12 inch long, 8 watt fluorescent bulbs. The translucent screen 14 disperses the light evenly through the transparent base of the viewing cell placed immediately above it. A bakery product such as a cake, donut, muffin, pastry or bread, is placed on the viewing cell.

A suitable camera 20 in FIG. 1 is, for instance, a Sony CCD video camera Model XC75 and the image is fed to a frame grabber computer card DT55LC-60 in a computer with monitor. The software used to analyze the image of the bakery product is Global Lab Image 3.0 from Data Translation Inc. or imaging software designed by Leco Inc.

FIG. 2 illustrates a substantially opaque cabinet 28 sized and shaped so that the imaging apparatus shown in the other figures may be placed inside and still be accessed and used. The cabinet 28 is used to eliminate or filter ambient light. Ambient light reflected off the bakery product could interfere with the capture of the image. The inside of the cabinet 28 is painted with flat black paint to prevent reflection.

The cabinet 28 includes a hinged door 30 attached to the front. The front door 30 covers upper and middle portions of the front of the cabinet 28. The opening 32 is provided in the lower portion of the front of the cabinet 28 to provide for placement and removal of the sample tray 36, see FIG. 3, over the translucent screen 14 of the light box 12 inside the cabinet 28. The front door 30 and the opening 32 are sized so that the door extends to a height just slightly above the combined height of the light box 12, light box cover 38 (see FIGS. 4A and 4B) and sample tray 36 when they are positioned inside the cabinet.

FIG. 3 illustrates an embodiment of a sample tray 36. The sample tray 36 includes a clear, light transmitting bottom. The bottom can be made of, for example, clear glass or plastic. Although not necessary, the side walls may also be made of clear, light transmitting material. Preferably as shown in FIG. 3, one end wall acts as a guide to permit easier and quicker placement of the sample tray 36 inside the cabinet 28 on the light box.

Figure 4B:
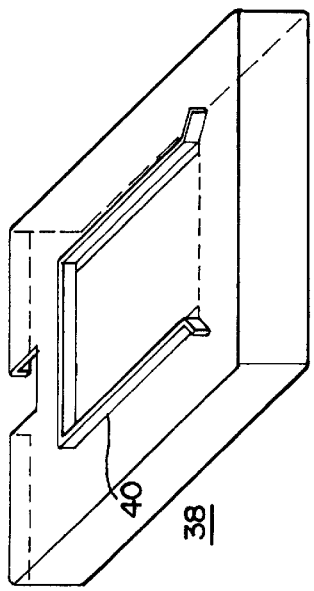

FIGS. 4A and 4B provided two views of a light box cover 38 which includes a sample tray guide frame 40. The light box cover is preferably made of an easily cleaned, scratch resistant light transmitting material such as hard plastic and prevents light box 12 from getting dirty or soiled with crumbs or the like.

The parameters of lighting intensity, camera distance, size of the viewing window are chosen with consideration of the type of bakery product and characteristics being measured and the desired results are optimized for image analysis. In order to capture an image, the light is adjusted so that the bakery product is lit sufficiently and in such a manner so that an appropriate image for the characteristics of interest can be obtained. For example, for measurement of the length, width and height, it is important to adjust the light so that the bakery product, and especially its edges, stands out against the surface on which it rests or against the background. If holes, grain or crust are of interest, it is important that the surface of the sample be sufficiently lit in order to make out these features in the captured image.

The image is analyzed to determine the desired characteristic of the bakery product such as width, height, area, porosity, volume, shape, hole and grain size, shape and distribution, and crust thickness. The image may typically depict the bakery product as a dark area on a white background if two dimensional measurements such as area or height are being measured. Alternatively, the image may be a picture of a cake surface for example where the grain is discernable for categorization and measurement. The methods of the present invention are useful with any bakery product where a specific measurement can be described and programmed within the software.

It may be necessary to cut the bakery product in a specific manner to obtain reproducible measurements with the imaging system. A suitable means of cutting a cake or other bakery product in a repeatable manner is with a miter box 42, FIGS. 5A and 5B. The bakery product may be placed on the cutting board surface of the miter box and positioned against the sides of the box. The knife is inserted in the slots and a cut made through the bakery product. Different slots could be used for different bakery products.

Illustrative embodiments of methods useful in the practice of the current invention will now be described for use in connection with and in reference to the illustrated apparatus. As with the illustrated apparatus, the described methods are only illustrative of the presently preferred methods and are not meant to be limiting or restrict the scope of the invention.

Figure 6A:
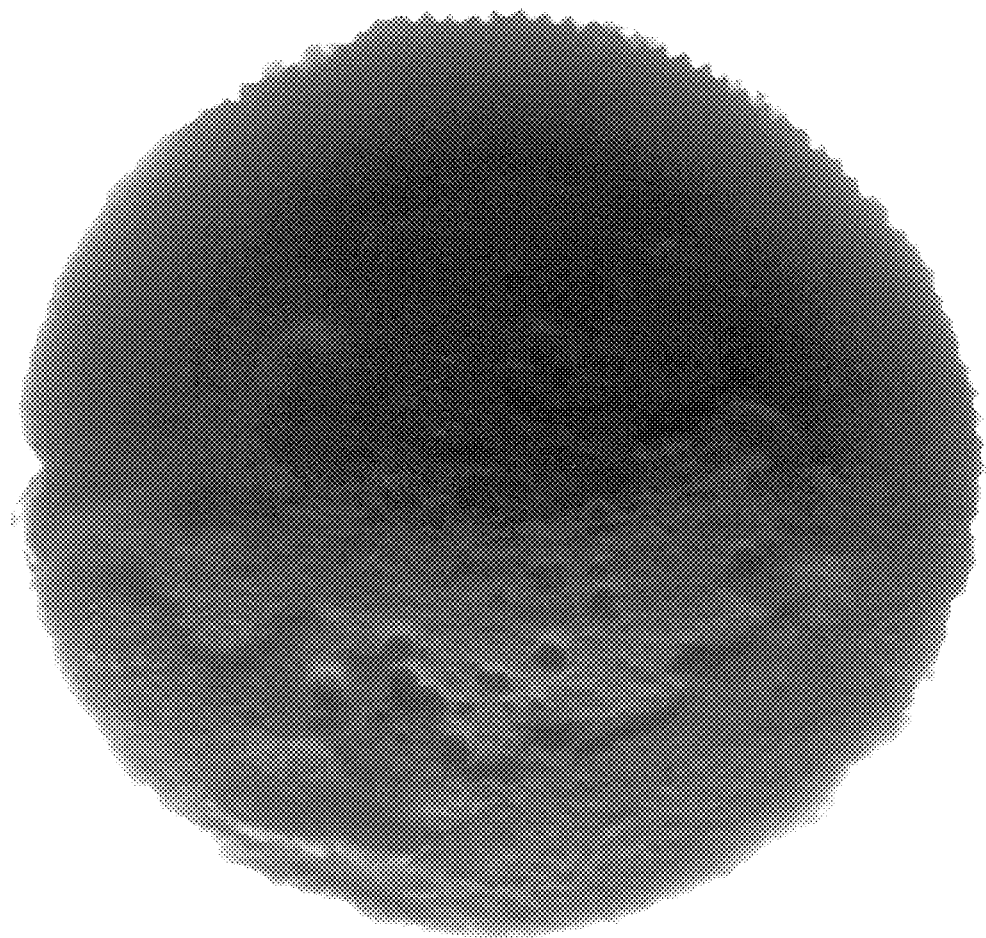
FIG. 6A is the captured image of the top of a round cake and FIG. 6B is a captured image of the side view of the same round cake.
Figure 6B:
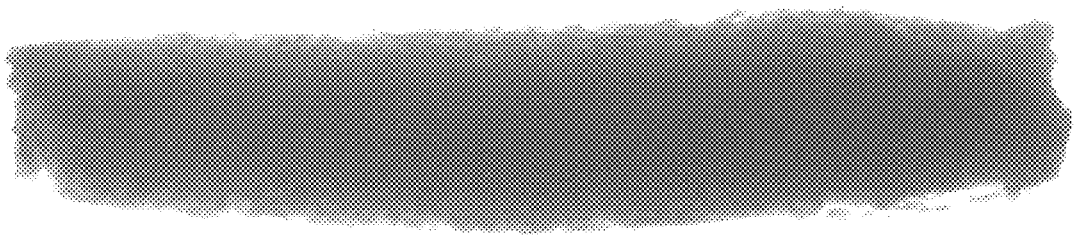

The volume of a 8" white round cake can be measured using the apparatus. A cake is placed in its natural baking position onto the viewing cell. The translucent screen disperses the light from beneath the viewing cell. The camera takes an image of the top of the cake as shown in FIG. 6A and the software measures the area of the cake surface using prescribed parameters of grayscale differentiation. The cake is then cut in a specific manner using a miter box specially prepared to facilitate exact duplication of the cut location for successive cakes. The slice cut from the cake is placed on its side on the screen and an image taken of the side of the cake as shown in FIG. 6B and the minimum radius measured by the software. The volume of the cake is calculated by multiplying the area by twice the minimum radius. The results of the measurements can be reported and the form of a report (for example, printed or on-screen, table or graph) can be selected by the user in accordance with the systems hardware and software.

A second example is computer imaging analysis of muffins for size and shape. The height, spread and shape of muffins is an important attribute for customer acceptance. It has been found that the preferred shape of muffins is distinctly different in different geographical areas of the USA. Typically muffin size is determined by ruler and shape is a subjective descriptive term such as "flat", "peaky" or "lopsided".

Figure 7A:
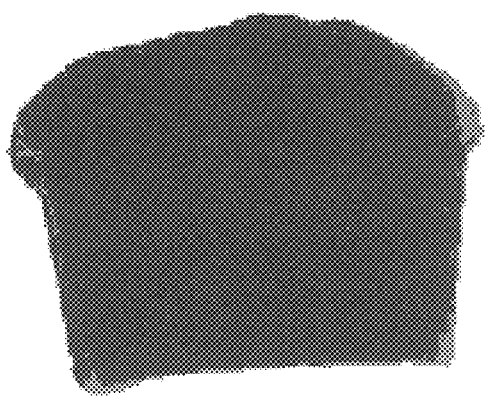
FIGS. 7A, 7B and 7C are the captured images of the side view of muffins.
Figure 7B:
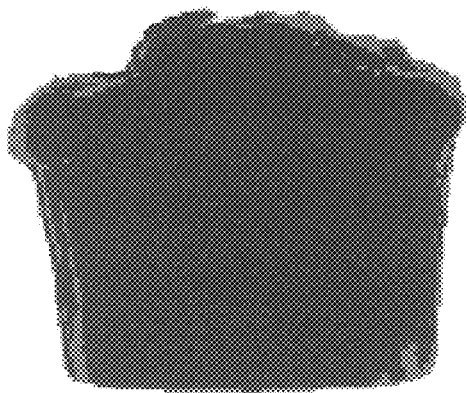
Figure 7C:
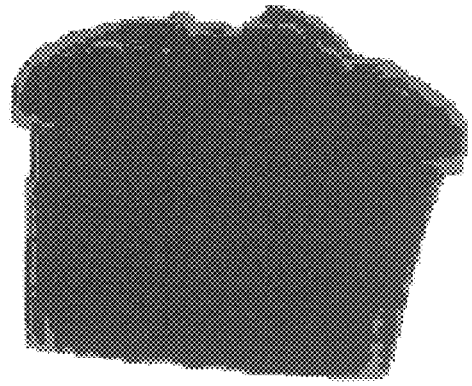

In this method, three muffins are cut in half and placed cut side down in the viewing cell as shown in FIGS. 7A, 7B and 7C. The lighting source and intensity, camera distance from the sample are set in a similar manner as for the 8" cake volume measurement and the muffins are typically depicted as dark areas on a white background. The software determines the major axis, minor axis, area, roundness and calculates the square of the perimeter divided by the area to define the shape and size of the muffins. These parameters have been found to be sufficient to provide a description of muffins that will quantify the size of the muffins and differentiate shape.

Figure 5A:
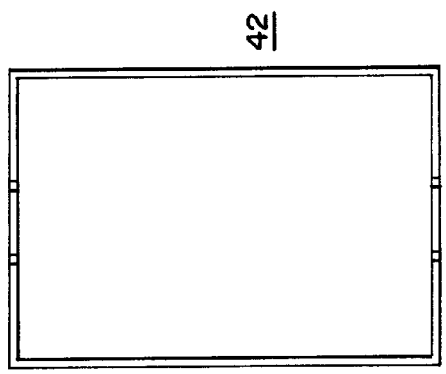
FIG. 5A is a front-side view and FIG. 5B is a top view of a miter box.
Figure 5B:
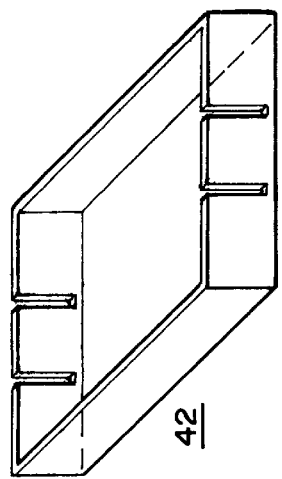
Figure 8A:
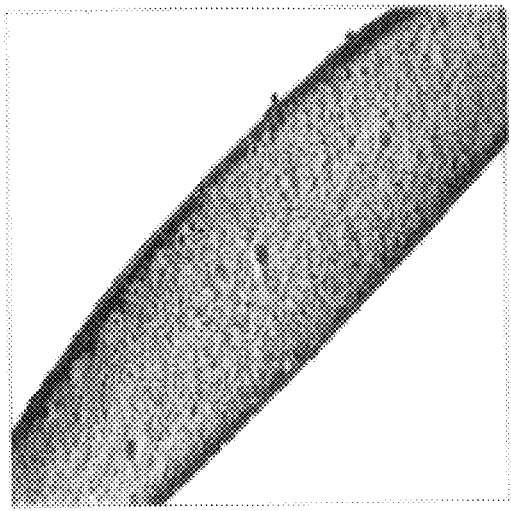
FIGS. 8A and 8B are the captured images of vertical cuts of a cake and FIGS. 8C and 8D are the captured images of horizontal cuts of a cake.
Figure 8B:
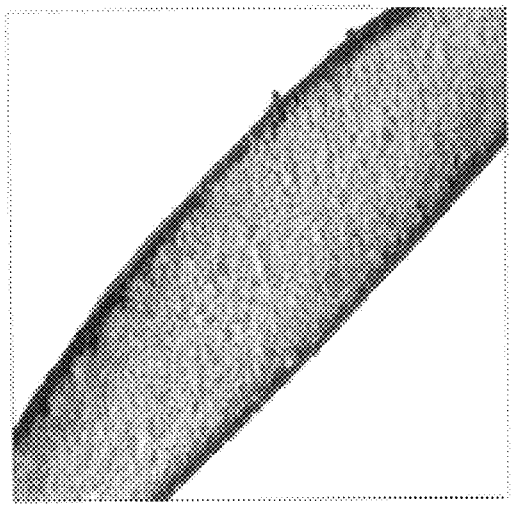
Figure 8C:
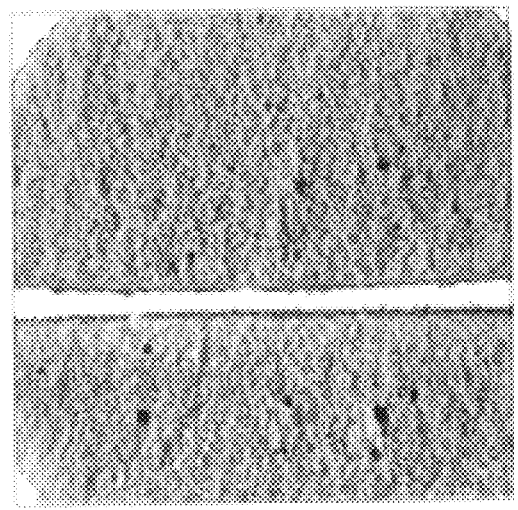
Figure 8D:
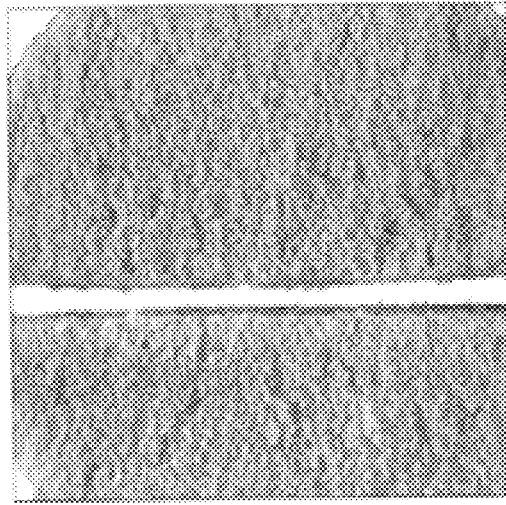

A third example is computer imaging analysis of the structure of a cake, referred to as grain. A vertical cross section is cut from the middle of the cake using a miter box such as shown in FIGS. 5A and 5B and the remaining portion of the cake is cut horizontally using a modified torte knife. The cake is set on a table top, the adjustable pegs on the torte knife set at a specific height, and the cake cut using a sawing motion keeping the pegs in contact with the table. The equipment used for cutting the cakes ensures level surfaces for the imaging analysis. The vertically cut, portions, see FIGS. 8A and 8B, of the cake are placed onto the viewing cell. An incident light source is shown on the surface of the cake creating dark shadows on the holes or grain of the cake and reflecting light off the cell walls. The parameters of lighting source and intensity, camera distance from the sample and size of the viewing area are optimized to give a clear sharp image. The horizontal cut portions, see FIGS. 8C and 8D, of the cake are placed onto the viewing cell and if necessary, the lighting and camera settings are readjusted to produce a good image. The software detects the grain based on grayscale range settings and can be further subdivided into size categories. The total grain area divided by the total area of the cake analyzed is reported as grain area %. This number corresponds to the porosity of the cake. A higher percentage signifies a more open grain. Information on individual grain hole sizes and shapes can also be reported. The results of the measurements can be reported and the form of a report (for example, printed or onscreen, table or graph) can be selected by the user in accordance with the systems hardware and software.

Similar grain analysis can be made on donuts. The donut is cut horizontally and placed cut side facing upwards on the viewing cell of the imaging system. See FIG. 9. The software measures the area of the donut which is the dark area in the image and the light area represents the center hole of the donut. These parameters in themselves can be used to quantify donut characteristics and describe donut attributes.

Figure 9:
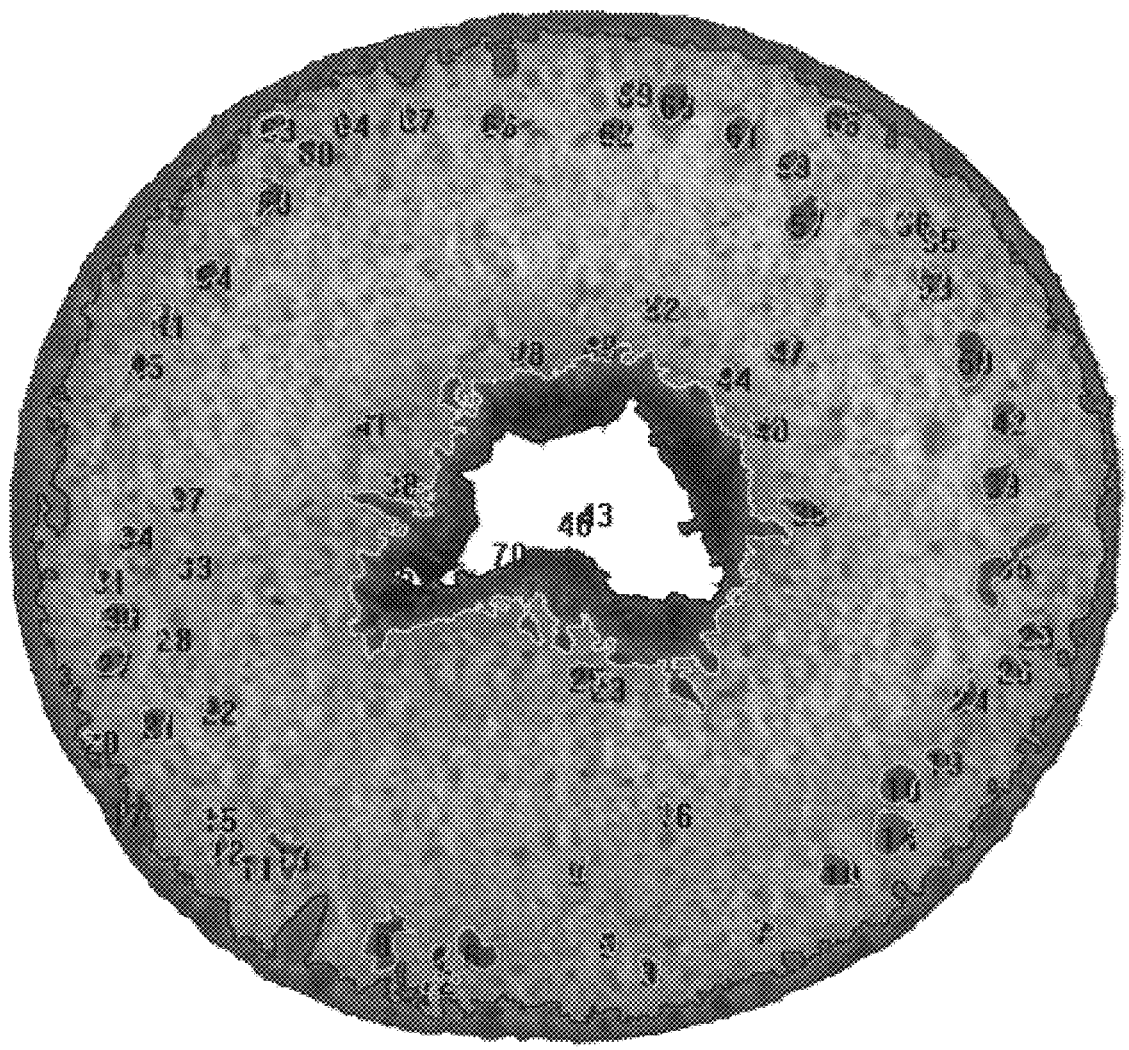
FIG. 9 is a captured image of a top view of a horizontally sliced donut.
Figure 10A:
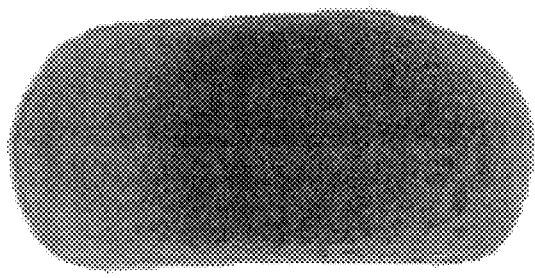
FIGS. 10A, 10B, 10C and 10D are the captured images of the side view of donuts.
Figure 10B:
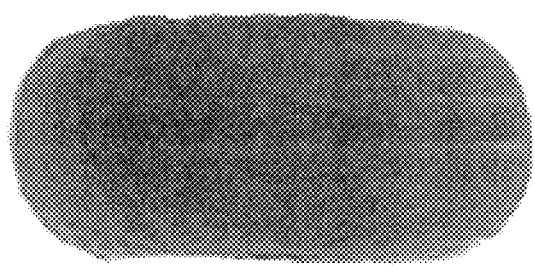
Figure 10C:
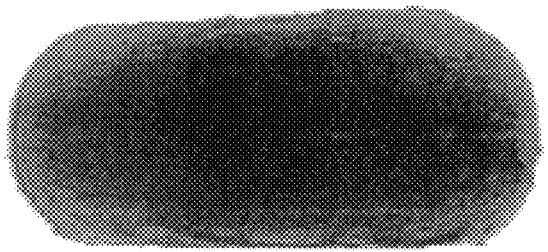
Figure 10D:
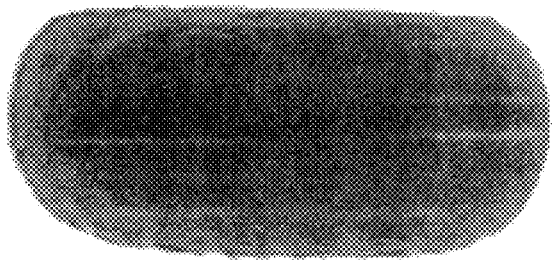

An incident light source is shone on the surface of the donut creating dark shadows on the holes of the donut and reflecting light off the cell walls as shown in FIG. 9. The parameters of lighting source and intensity, camera distance from the sample and size of the viewing area are optimized to give a clear sharp image. The software detects the holes and crust based on grayscale range settings and can be further subdivided into size categories. The total area of the holes is reported as area % and the crust can also be reported as area %. Information on individual hole sizes and shapes can also be reported. The results of the measurements can be reported and the form of a report, (for example, printed or on-screen, table or graph) can be selected by the user in accordance with the systems hardware and software.

A further example is the computer image analysis of the size of a donut. Four cake or raised donuts are cut in half and placed on the viewing cell with the cut surfaces on the viewing screen. The parameters of lighting source and intensity, camera distance from the sample and size of the viewing area are optimized to give a clear sharp image. See FIGS. 10A, 10B, 10C and 10D. The image typically depicts the donut as a dark area and the tray as a white area. The software measure the height and width of the donut and the results are reported.

Although illustrative embodiments of the invention have been shown and described, it is to be understood that various modifications and substitutions may be made by those skilled in the art without departing from the spirit and scope of the present invention.

What is claimed is:

1. A method for determining the approximate volume of a bakery product using computer imaging comprising:

placing a bakery product in a lighted field so that there is sufficient contrast between the bakery product and the supporting surface on which the bakery product is placed in order that computer imaging software may distinguish between the bakery product and the support surface;

capturing an image of the bakery product in the field such that the area of the bakery product can be determined from the image;

making a vertical slice in the bakery product;

placing a vertical slice of the bakery product in the lighted field;

capturing an image of the vertical slice of the bakery product; and calculating the volume of the bakery product based upon the captured images of the bakery product and of the vertical slice of the bakery product.

2. The method of claim 1 further comprising providing viewable images of the first bakery product.

3. The method of claim 1 further comprising comparing one or more of the volume, height, width, minimum radius, minor axis or area with prescribed specifications.

4. The method of claim 1 further comprising performing the steps of claim 1 on a plurality of bakery products in order to determine whether they meet prescribed specifications for one or more of the volume, height, width, minimum radius, minor axis, area and are substantially uniform.

5. The method of claim 1 in which the bakery product is a cake.

6. A method for determining the approximate size and shape of a bakery product using computer imaging comprising:

making at least one vertical slice of a bakery product;

placing a vertical slice of a bakery product in a lighted field so that there is sufficient contrast between the bakery product and the supporting surface on which the bakery product is placed in order that computer imaging software may distinguish between the bakery product and the supporting surface in captured images;

capturing an image of the vertical slice of a bakery product; and determining the length of the major axis, length of the minor axis, area, roundness and calculating the square of the perimeter divided by the area using the captured image of the vertical slice of bakery product.

7. The method of claim 6 further comprising providing a viewable image of the vertical slice of bakery product.

8. The method of claim 6 further comprising comparing one or more of the length of the major axis, length of the minor axis, area, roundness, or square of the perimeter divided by the area with prescribed specifications.

9. The method of claim 6 further comprising performing the steps of claim 6 on a plurality of bakery products in order to determine whether they meet prescribed specifications for one or more of the length of the major axis, length of the minor axis, area, roundness and square of the perimeter divided by the area and are substantially uniform.

10. The method of claim 6 wherein the bakery product is a muffm.

11. A method for determining the grain of bakery product using computer imaging comprising:

making a slice in a bakery product in such a manner as to expose the internal grain;

illuminating the exposed internal grain of the bakery product in such a manner that computer imaging software may distinguish grain holes;

capturing an image of the exposed internal grain of a bakery product and determining a grain area; and calculating the porosity of the bakery product by dividing said grain area by the total area of the bakery product.

12. The method of claim 11 further comprising determining the sizes and shapes of grain holes.

13. The method of claim 1 further comprising providing a viewable image showing the grain of the bakery product.

14. The method of claim 11 further comprising comparing the porosity with a prescribed specification.

15. The method of claim 11 further comprising performing the steps of claim 11 on a plurality of bakery products in order to determine if they meet a prescribed specification for porosity and are substantially uniform.

16. The method of claim 11 wherein the bakery product is selected from the group consisting of cakes, donuts, muffins, pastries or bread.

17. A method for determining the area of holes and crust of a bakery product using computer imaging comprising:

cutting a slice at or near the midsection of a baked bakery product;

illuminating the cut surface of the slice in such a manner that computer imaging software may distinguish holes and baked crust;

capturing an image of the cut surface of the slice; and determining the area of the holes of the bakery product and the area of the crust of the bakery product.

18. The method of claim 17 further comprising making one or more additional slices in the bakery product; illuminating the cut surface of one or more of the additional slices in such a manner that computer imaging software may distinguish holes and crust and capturing one or more images of the cut surfaces of the additional slices.

19. The method of claim 17 further comprising calculating the porosity of the bakery product.

20. The method of claim 17 further comprising providing a viewable image of the holes and crust of a bakery product.

21. The method of claim 17 further comprising determining the sizes and shapes of the holes of a bakery product.

22. The method of claim 17 further comprising comparing one or more of the area of the holes, area of the crust, size of the holes, or the shapes of the holes with prescribed specifications.

23. The method of claim 17 further comprising preforming the steps of claim 17 on a plurality of bakery products in order to determine whether they are substantially uniform and meet prescribed specifications for one or more of area of the holes, area of the crust, size of the holes, or shapes of the holes.

* * * * *

UNITED STATES PATENT AND TRADEMARK OFFICE
CERTIFICATE OF CORRECTION

PATENT NO. : 6,201,885 B1  Page 1 of 1
DATED : March 13, 2001
INVENTOR(S) : Hodgson et al.

It is certified that error appears in the above-identified patent and that said Letters Patent is hereby corrected as shown below:

Column 4,
Line 20, after "distance," insert -- and --.

Column 5,
Line 6, after "minimum radius" insert -- is --.
Line 42, after "vertically cut" delete","".

Signed and Sealed this

First Day of January, 2002

Attest:

JAMES E. ROGAN
Attesting Officer    Director of the United States Patent and Trademark Office